(12) United States Patent
Merchant et al.

(10) Patent No.: US 6,544,395 B1
(45) Date of Patent: Apr. 8, 2003

(54) SYSTEM FOR THE APPLICATION OF SAMPLES ON A SUBSTRATE

(75) Inventors: Mark E. Merchant, Nederland, TX (US); Philip A. Guadagno, Vidor, TX (US); Robert J. Sarrine, Beaumont, TX (US); Suzan Robinson, Silsbee, TX (US); James Robert Markus Sanford, Mauriceville, TX (US); Henry Garsee, Kountze, TX (US); Eric H. Petersen, Beaumont, TX (US); Tipton L. Golias, Beaumont, TX (US)

(73) Assignee: Helena Laboratories Corporation, Beaumont, TX (US)

( * ) Notice: Subject to any disclaimer, the term of this patent is extended or adjusted under 35 U.S.C. 154(b) by 0 days.

(21) Appl. No.: 09/180,320

(22) PCT Filed: May 5, 1997

(86) PCT No.: PCT/US97/07696

§ 371 (c)(1),
(2), (4) Date: Jul. 15, 1999

(87) PCT Pub. No.: WO97/42496

PCT Pub. Date: Nov. 13, 1997

Related U.S. Application Data

(60) Provisional application No. 60/016,933, filed on May 6, 1996.

(51) Int. Cl.⁷ .................... G01N 27/26; G01N 27/447; G01N 1/10; B01L 11/00
(52) U.S. Cl. ................. 204/467; 204/456; 204/466; 204/606; 204/616; 204/618; 422/100; 436/180
(58) Field of Search ................. 204/456, 466, 204/467, 606, 616, 617, 618; 422/100; 436/180

(56) References Cited

U.S. PATENT DOCUMENTS

| | | | |
|---|---|---|---|
| 5,137,614 A | * | 8/1992 | Golias .................. 436/516 |
| 5,972,188 A | * | 10/1999 | Rice et al. ............ 204/456 |

FOREIGN PATENT DOCUMENTS

| | | | |
|---|---|---|---|
| WO | WO 96/27787 | * | 9/1996 |
| WO | WO 99/12025 | * | 3/1999 |

* cited by examiner

Primary Examiner—Jill Warden
Assistant Examiner—John S. Starsiak, Jr.
(74) Attorney, Agent, or Firm—Piper Rudnick LLP; Jerold I. Schneider

(57) ABSTRACT

Novel apparatuses and methods for depositing or placing substances on substrates or plates are described. The invention relates to automated and semiautomated apparatuses and methods for controlled volume and precise placement of substances on substrates. Combinations of applicator tips, applicator tip assemblies, applicator reservoirs, applicator holders and movable racks precisely and accurately place samples and testing chemicals on substrates. Applicator tips particularly useful for dunk transfer and deposit processes and for carrying substances are disclosed. Apparatuses for precisely moving applicator holders, applicator reservoirs and tips are disclosed. The methods and apparatuses also have features for pre-loading substances on applicators and applicator reservoirs and precisely delivering the preloaded substances to substrates.

58 Claims, 13 Drawing Sheets

← TIP BOTTOM

← TIP BOTTOM

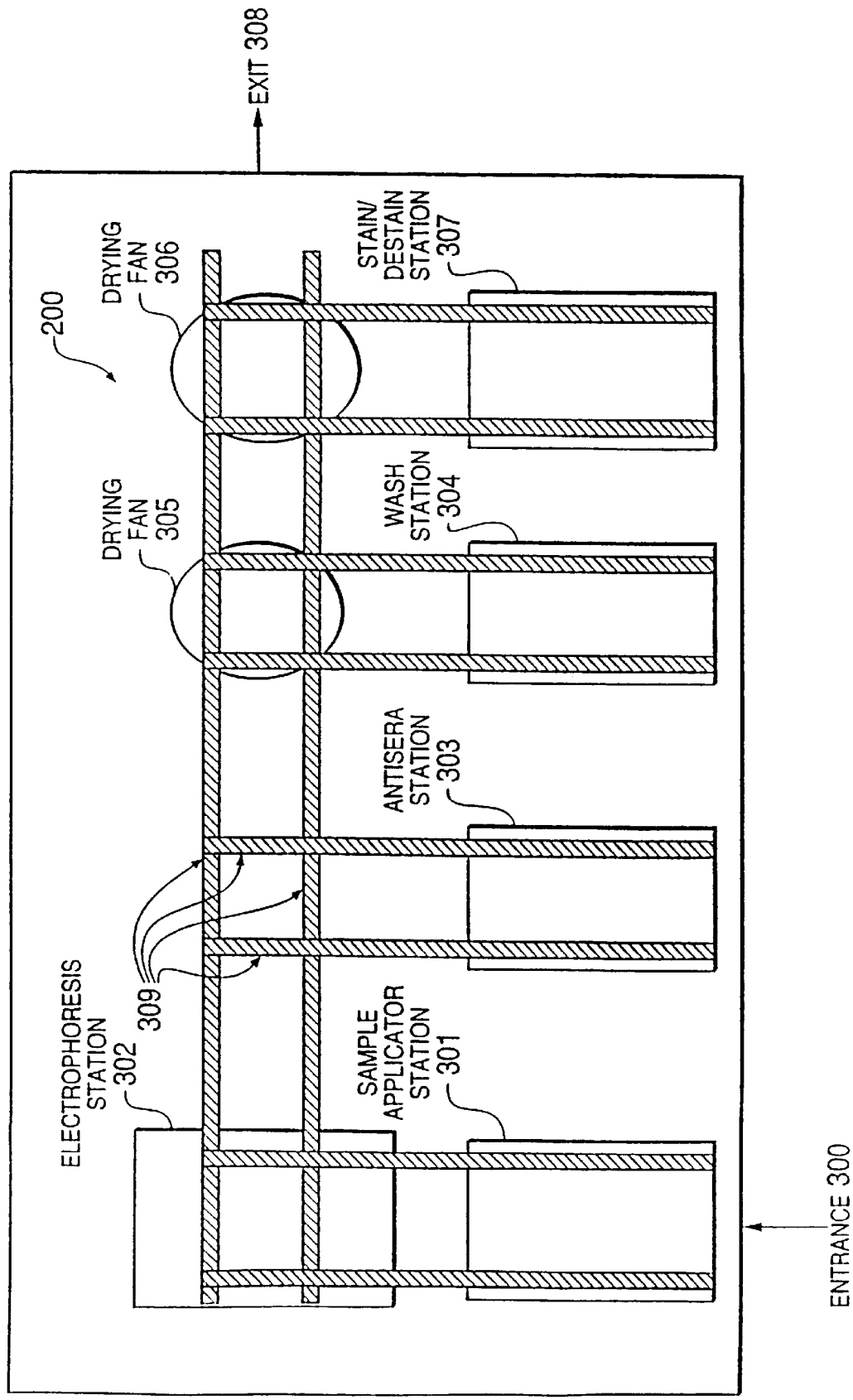

SYSTEM FOR THE APPLICATION OF SAMPLES ON A SUBSTRATE

RELATED APPLICATIONS

This application claims the benefit of U.S. Provisional Application No. 60/016,933, filed May 6, 1996, which is hereby incorporated by reference.

TECHNICAL FIELD

This invention is in the medical and chemical related field. The invention relates to the placing of samples on a substrate.

BACKGROUND

Scientists and medical technicians are constantly searching for better ways to place, transfer and/or apply samples on various substrates for testing or diagnostic-type purposes. The placement, volume, and dimensions of such samples on a substrate are important to the results of the procedures carried out on the samples. In some instances, improper application of the samples on a substrate will significantly alter or destroy the test results. One such procedure, which is subject to poor results based upon the application of samples, is the procedure of zone electrophoresis. For further background on electrophoresis see, for example, U.S. Pat. No. 5,137,614, issued to Golias on Aug. 11, 1992, entitled "IMMUNOFIXATION ELECTROPHORESIS CONTROL SYSTEM" and incorporated herein by reference.

For further background on the application of biological samples for an electrophoresis process, see U.S. Pat. No. 5,405,516, issued to Bellon on Apr. 11, 1995, entitled APPARATUS FOR THE APPLICATION OF BIOLOGICAL SAMPLES TO AN ELECTROPHORETIC SLAB SUPPORT, herein incorporated by reference.

Present methods for the automatic application of samples, especially fine samples, to a substrate or flat surface are inadequate.

It is an object of the invention improve upon the methods and devices for depositing samples or fluids on a substrate.

It is an object of the invention to control the amount of fluid applied to a substrate.

It is an object of the invention to control the footprint or shape of the fluid applied to a substrate.

It is an object of the present invention to strive to produce a nearly two dimensional deposit of fluid onto a substrate.

It is an object of the present invention to provide a semi-automatic and automatic method and device for placing fluid on a substrate.

It is an object of the present invention to reduce the risks of damaging the applicator or the substrate during a deposit or delivery.

SUMMARY OF THE INVENTION

The novel methods and apparatuses for depositing or placing substances on substrates disclosed include applicator tips, applicator reservoirs, applicator tip assemblies, automated and semiautomated apparatuses and processes for using applicators. The methods and other apparatuses are used to automatically or semiautomatically place controlled amounts of substances on substrates. Combinations of applicator tips, applicator tip assemblies, applicator reservoirs, applicator holders and movable racks precisely and accurately place samples and testing chemicals on substrates. Racks and other equipment are used to bring the applicators or transferred substances into contact with the substrates. Preferably racks with vertical movement are used to precisely deposit samples and fluids.

Specifically, methods and hardware for applicator tips which carry and deposit sample fluid using lyophilic surfaces are disclosed. Generally, the tips are formed in two parts, one part carries sample fluid and the second part does not. Barriers and other techniques are used to prevent the second part of the tips from carrying fluid. The tips are mounted on applicator holders which are placed on racks and used in automatic and semiautomatic processes.

Applicator reservoirs can be used to pre-load substances or fluids for later transfer to substrates. The reservoirs deposit or place controlled volumes of substances or fluids on substrates or plates. The preferred method mixes fluids with polymers to form a gel which is cast in a reservoir. The gel is then placed in contact with a substrate to deposit the fluid. Preferably, these reservoirs are connected to applicator holders which are used in combination with racks and other delivery apparatus.

BRIEF DESCRIPTION OF THE DRAWINGS

FIG. 20 is a top view of an automated immuno-fixation electrophoresis system.

DETAILED DESCRIPTION OF THE PREFERRED EMBODIMENT

I. Introduction

The present invention is a method and apparatus for supporting immuno-fixation electrophoresis or any other type of testing which requires precise and accurate sampling. Generally, the system comprises an application station with a fluid applicator, a chemical delivery system or station with a chemical delivery applicator and a substrate.

Generally, the fluid applicator retains a fluid sample for deposit onto a substrate. The application station is a semi-automatic or automatic device for insuring precise deposit of the fluid sample on a substrate. The chemical delivery system applies chemicals or substances to a substrate, and the substrate is the medium for facilitating successful test results.

II. Major Subsystems

A. Fluid Applicator

Figure 1:
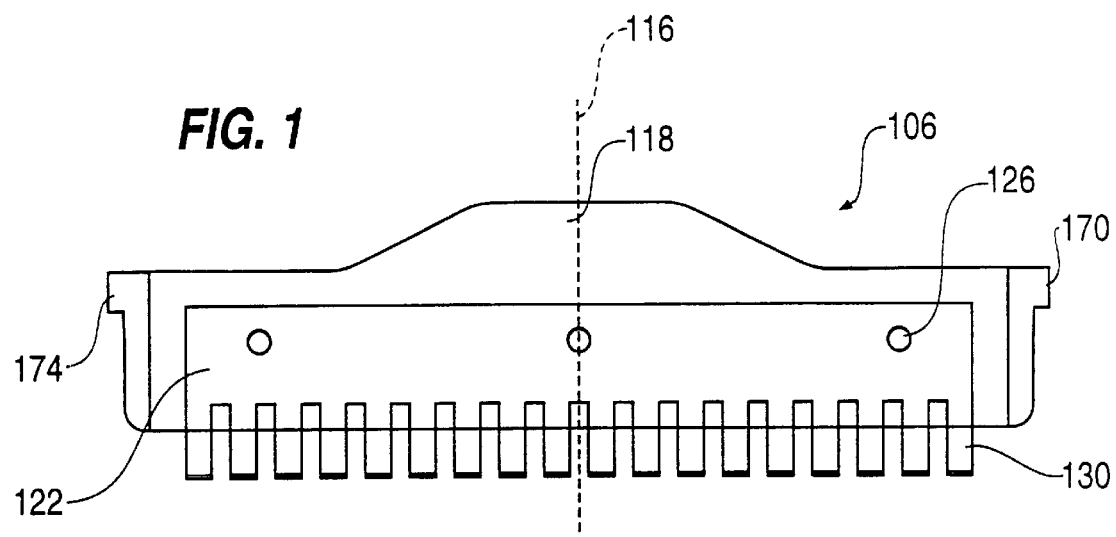
FIG. 1 is a front view of the fluid applicator.

FIG. 1 shows a front view of a fluid applicator 106. The fluid applicator 106 comprises an applicator holder 118 and a multiple applicator tip assembly 122 with applicator tips 130. The applicator tips 130 extend beyond the bottom of the applicator holder 118.

The applicator holder 118 is made of a sturdy material, preferably plastic. Typically, the plastic is styrene. The body of the applicator holder 118 includes a right guide 170, left guide 174, and three pins 126. The two guides 170, 174 are used to align the applicator holder 118 within an application station for automatic or semi-automatic application. In the preferred embodiment, one of the guides is wider than other guide to insure the applicator holder 118 is properly inserted into an application station. In alternative embodiments, any difference in the two guides' shape or size can accomplish the same result. If the applicator tip 130 configuration is symmetrical around the central axis 116, the guides 170, 174 may be identical.

The three pins or snaps 126 on the applicator holder 118 are used to attach the multi-applicator tip assembly 122 to the applicator holder 118. The three pins 126 protrude from the applicator holder 118. The pins 126 may be circular, square, elliptical, or any other shape. The number and position of the pins 126 may vary. In a preferred embodiment, the pin heads are larger than their base. Thus, the multiple applicator tip assembly 122 is attached by aligning holes in the assembly 122 with each pin, and snapping the assembly 122 onto the applicator holder 118.

In alternative embodiments, there are a variety of ways to firmly attach the applicator holder 118 and the multiple applicator tip assembly 122. For example, they could be attached using double sided tape, heat or ultrasonic sealing, or any common type of adhesive, such as glue. In these embodiments, the holder preferably has a slot or groove to insure the applicator tips 130 are properly positioned.

Figure 2:
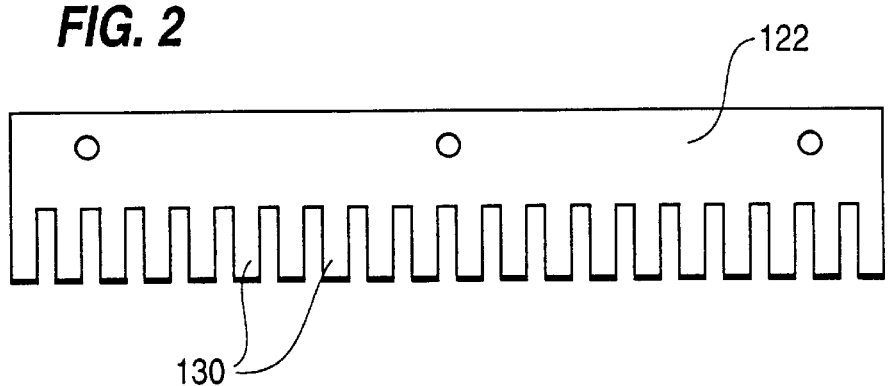
FIG. 2 is a front view of a multiple applicator tip assembly.

FIG. 2 shows the multiple applicator tip assembly 122. In the preferred embodiment, the multiple applicator tip assembly 122 is approximately 4½ inches long, 1 inch high, and the width of a piece of paper. The width of the assembly is important because, ideally, immuno-fixation electrophoresis desires a two dimensional line of biological fluid placed on the substrate. The two dimensional line should have a length direction perpendicular to the direction of electrophoretic movement, a depth dimension into the substrate at right angle to the direction of electrophoretic movement, and the smallest possible width dimension. These dimensions directly affect the accuracy of the test results.

Figure 3:
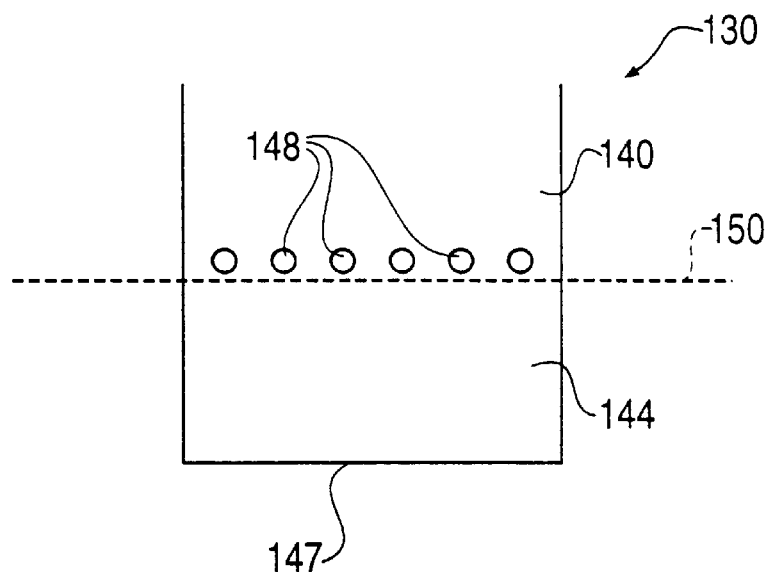
FIG. 3 is an enlarged view of an applicator tip.

FIG. 3 shows a single applicator tip 130. The applicator tip 130 comprises a first portion 140, second portion 144, and a blade 147. The second portion 144 is designed to retain fluid. The first portion 140 is designed to create a barrier 150 which limits the amount of fluid deposited by the applicator tip 130. The barrier 150 may also be created by the physical or chemical characteristics of the second portion 144. In alternative embodiments, the barrier 150 limits the amount of fluid retained.

In the preferred embodiment, the applicator tip 130 retains fluid from the barrier 150 to the blade 147. This distance is usually within the range of 0.05 through 0.50 mm. In the preferred embodiment this distance is approximately 0.18 mm. The distance is small because, the smaller the amount of fluid retained by the applicator tip 130, the easier it is for the fluid applicator 106 to precisely deposit the fluid on the substrate. The barrier 150 can take a variety of forms, such as physical, chemical, electrical, or any combination of these techniques.

Some of the common physical barriers 150 are apertures, holes, perforations 148, or changes in the texture of the surface. These holes 148 may be circular, elliptical, or any other shape. In the preferred embodiment six holes or perforations 148 are placed approximately at 0.018 inches above the blade 180 on the applicator tip 130. The holes 148 are preferably approximately 0.006 inches in height and oval in shape. The holes 148 are horizontally aligned near the bottom of the applicator tip 130. The holes 148 create a physical barrier 150 to the fluid which prevents the applicator tip 130 from retaining fluid above the holes 148. This applicator configuration prevents too much fluid from being retained at the ends of the applicator tip 130 and allows the applicator tip 130 to bend in the vertical and horizontal planes.

Figure 4:
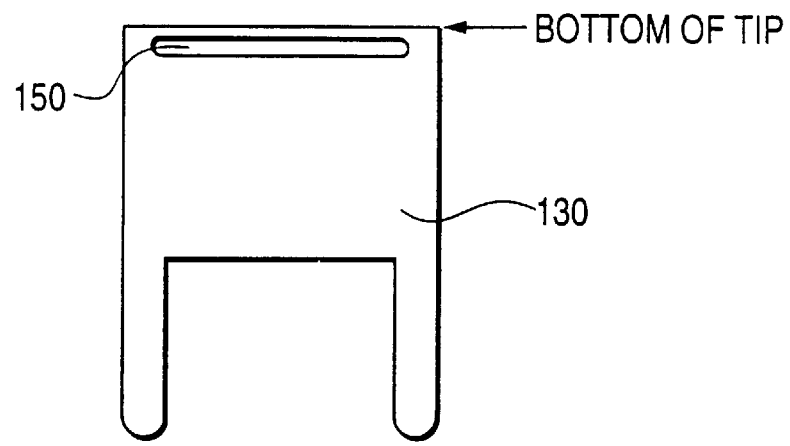
FIGS. 4–11 are enlarged views of different applicator tip configurations.
Figure 5:
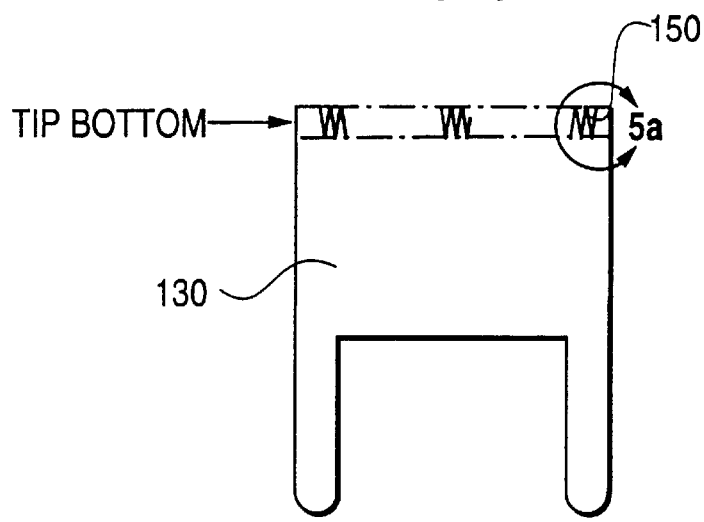
Figure 5A:
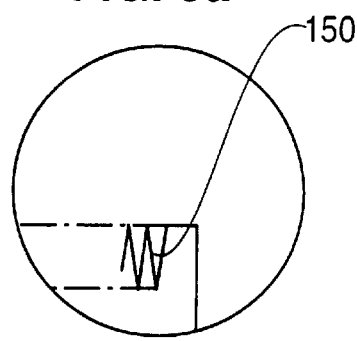
Figure 6:
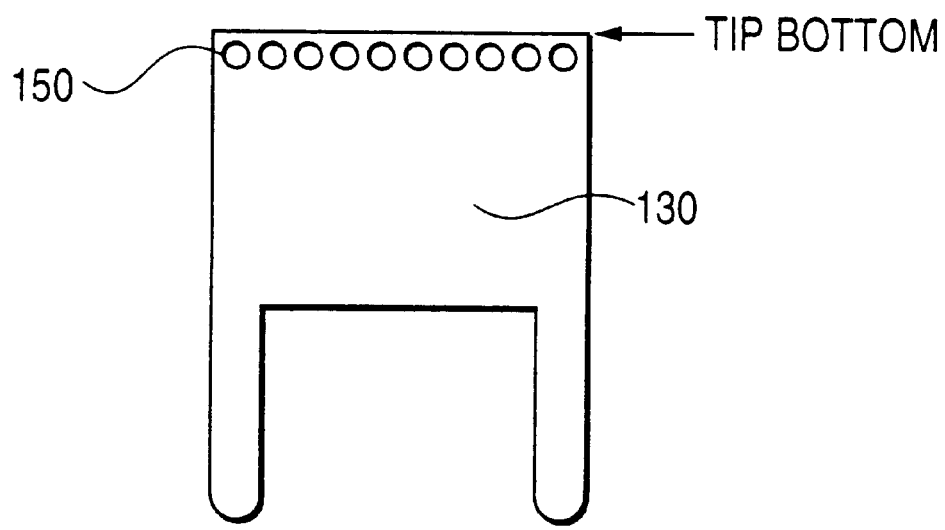
Figure 7:
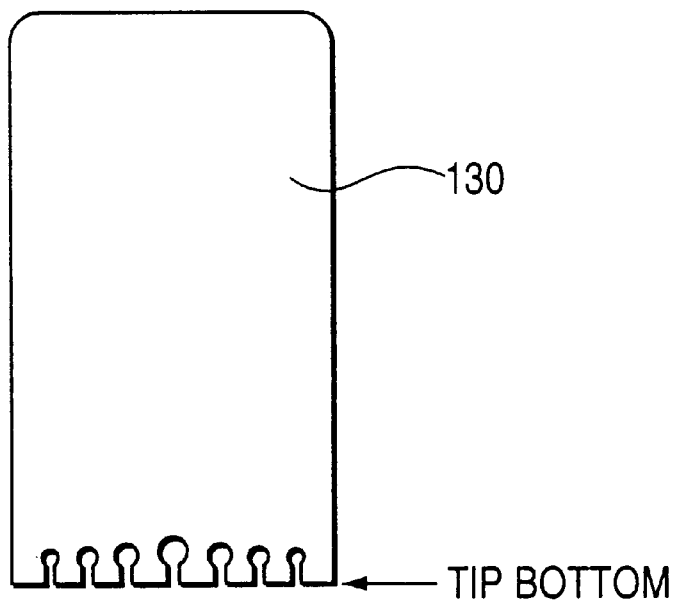
Figure 8:
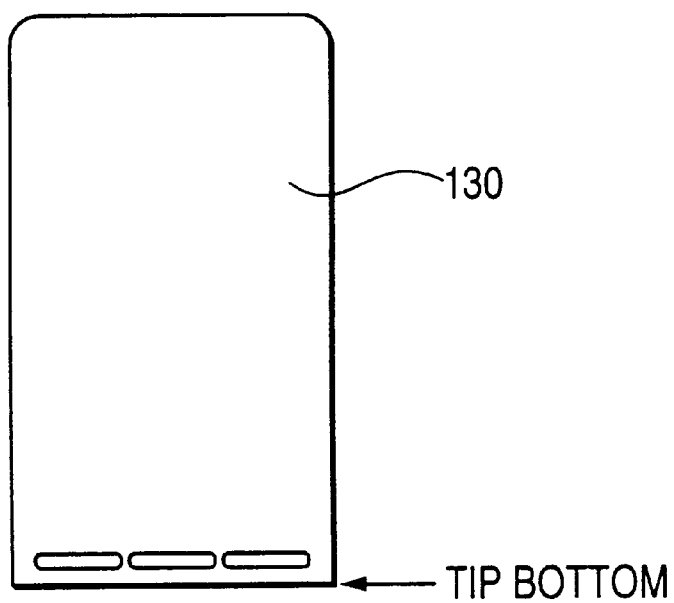
Figure 9:
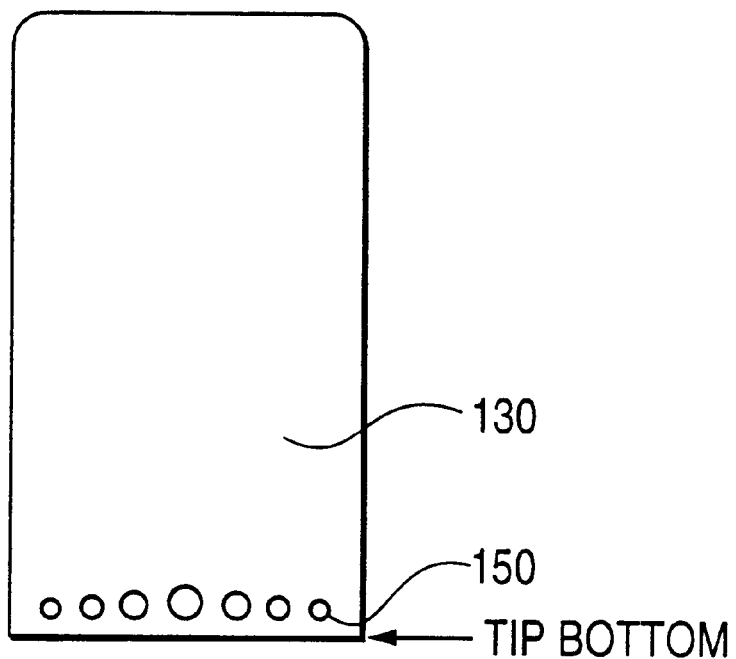
Figure 10:
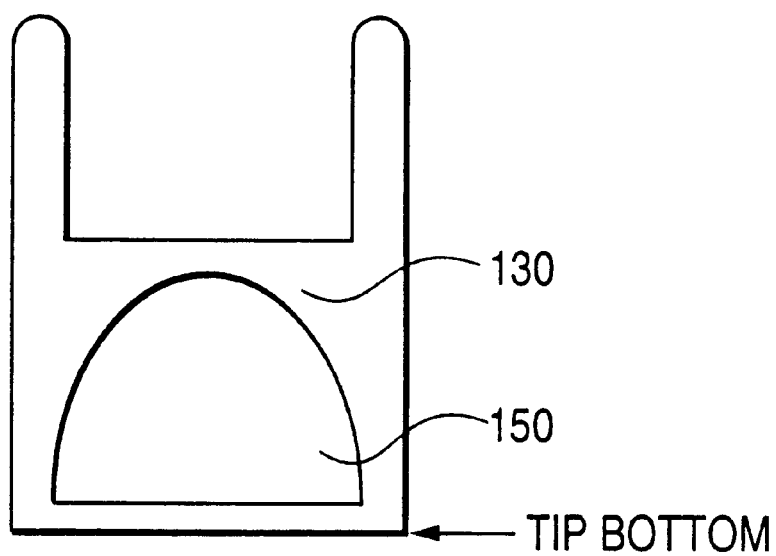

FIGS. 4–10 show a variety of different applicator tip 130 configurations. FIG. 4 shows an applicator tip 130 with a physical barrier 150 (i.e. the horizontal opening) just above the blade 147. FIG. 5 shows an applicator tip 130 with serrated teeth. FIG. 6 shows an applicator tip 130 with a physical barrier 150 created by a horizontal row of closely spaced circular openings. FIG. 7 shows an applicator tip 130 with "key hole shape" openings evenly spaced along the bottom of the tip 130. The "key hole shape" openings are tallest in the middle and become progressively smaller toward the ends. FIG. 8 shows an applicator tip 130 with three horizontal openings just above the bottom. FIG. 9 shows an applicator tip 130 with a row of circular openings just above the bottom of the tip 130. The circular openings are largest at the middle and become progressively smaller toward the ends. FIG. 10 shows an applicator tip 130 with a "mouse hole" shaped opening. Any of these applicator tips 130 may be disposable.

A physical barrier 150 may also be created by making the first portion 140 of the applicator tip 130 rough or texturized. Rough or texturized surfaces have lyophobic characteristics. Thus, if the first portion 140 of the applicator tip 130 has a rough surface, the rough surface prevents the applicator tip 130 from retaining the fluid sample above the barrier 150.

Some common chemical or electrical barriers 150 are created by using an applicator tip 130 with specific lyophobic or lyophilic characteristics or chemically treating the surface. For example, if the first portion 140 of an application tip 130 is made of a lyophobic substance and the second portion 144 is made of a lyophilic substance, only the second portion 144 of the applicator tip 130 will retain fluid. To achieve these results, the first portion 140 should have lyophobic characteristics sufficient to generally prevent it from retaining the fluid sample, and the second portion 144 should have lyophilic characteristics sufficient to generally retain the fluid sample. These results can also be obtained by coating the surface of the applicator tip 130 with chemicals which causes the first portion 140 to posses the necessary lyophobic characteristics and the second portion 144 to possess the necessary lyophilic characteristics.

Figure 11:
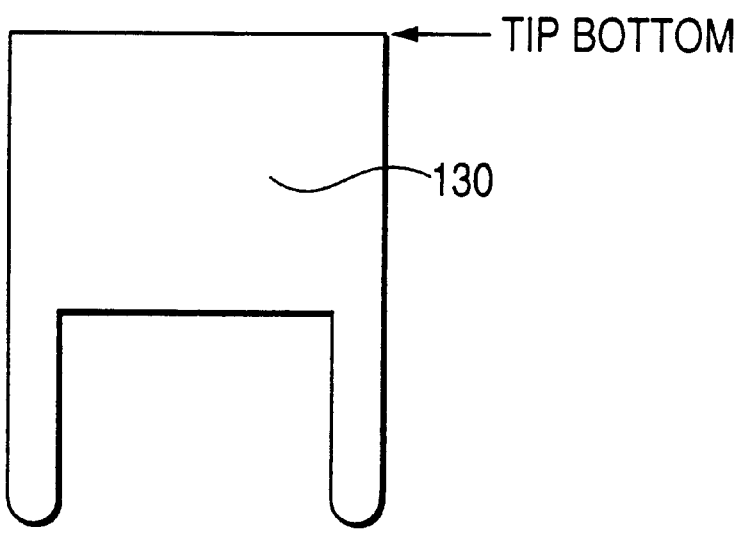

FIG. 11 shows an applicator tip 130 suitable for a chemical or electrical barrier. Some of the techniques for altering the lyophobic or lyophilic characteristics of a portion of the applicator tip 130 are: electrically (corona discharge), chemically (hydrophilic polymer-natural or synthetic) and/or, as stated above, mechanically (abrading or perforating the surface).

The preferred technique for creating a chemical barrier 150 is to make the applicator tip 130 out of polyester or nylon, which passes the necessary lyophobic characteristics for the first portion 140, and create the second portion 144 of the applicator tip 130 by metalizing the polyester surface.

The end of the applicator tip 130 is called the blade 147, as shown in FIG. 3. The blade 147 is generally a smooth flat edge. In the preferred embodiment, the blade 147 possesses the same lyophilic characteristics as the second portion 144 of the applicator tip 130 so that the fluid sample adheres uniformly to the blade 147 and second portion 144.

In one embodiment, the blade 147 is that portion of the applicator tip 130 which contacts the substrate or plate 110, and thus, initiates the deposit of the retained fluid onto the substrate. In this embodiment, the retained fluid is released onto the substrate because the contact between the blade 147 and the substrate breaks the surface tension of the retained fluid. In this embodiment, the blade 147 should contact the substrate in a manner to prevent puncturing or damaging the substrate.

In an alternative embodiment, the blade 147 may never contact the substrate. For example, the retained fluid may be released when the retained fluid attached to blade 147 contacts the substrate.

In addition to the multiple types of applicator tip 130 configurations, there are many different ways to use the applicator tips 130, individually or in combination. For example, some applicator holders 118 may use a single applicator tip 130, while others may use a plurality of applicator tips 130. The single applicator tips 130 may also be combined to resemble a multiple applicator tip assembly 122. In the preferred embodiment, many applicator tips 130 are permanently connected to form a multiple applicator tip assembly 122.

Moreover, multiple fluid applicators 106 can also be combined to form a cartridge (not shown). Cartridges may be used to connect applicator holders 118 for loading into the applicator rack 540. Preferably the cartridges are made of plastic and hold three or more applicator holders. Use of the cartridges makes the loading and unloading of the applicators in the rack a quick and simple task.

Figure 12:
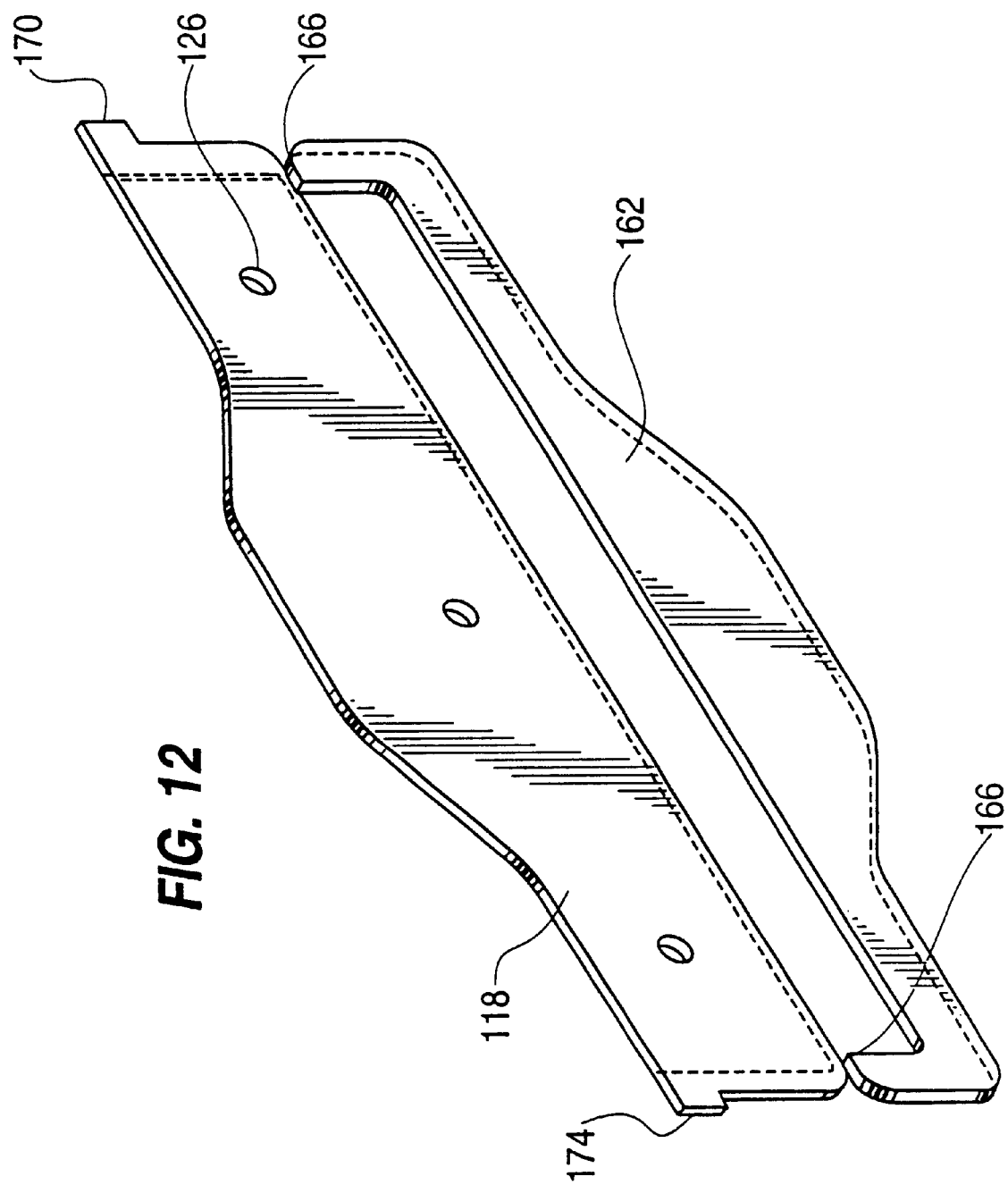
FIG. 12 is a perspective view of an applicator holder with a guard.

FIG. 12 shows an applicator holder 118 with a guard 162 to protect the applicator tips 130 from damage during manufacture, transport, packaging, etc. The applicator guard 162 is removed or snapped off from the applicator holder 118 at a break point 166 at either end of the applicator holder 118. The multiple applicator tip assembly 122 is not shown in FIG. 12.

Figure 13:
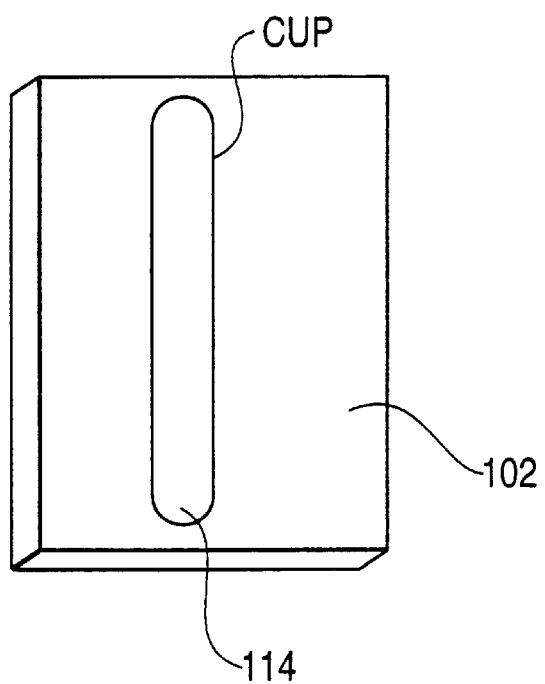
FIG. 13 is a top view of a single channel supply tray.

The fluid applicator 106 acquires the fluid sample from a supply tray. As shown in FIG. 13, a supply tray 102 may have a single channel 114 for holding fluid. The channel 114 may be any length. For example, if the channel 114 is built to service a fluid applicator 106 with a single applicator tip 130 the channel will be short. If the supply tray 102 or channel 114 is built to service a multiple applicator tip assembly 122, the channel 114 will be long enough to accommodate the insertion of all the applicator tips 130 simultaneously. A supply tray 102 is generally made out of plastic or metal. When used for immuno-fixation electrophoresis, the sample stored in the supply tray 102 is usually a biological fluid, such as blood.

Figure 14:
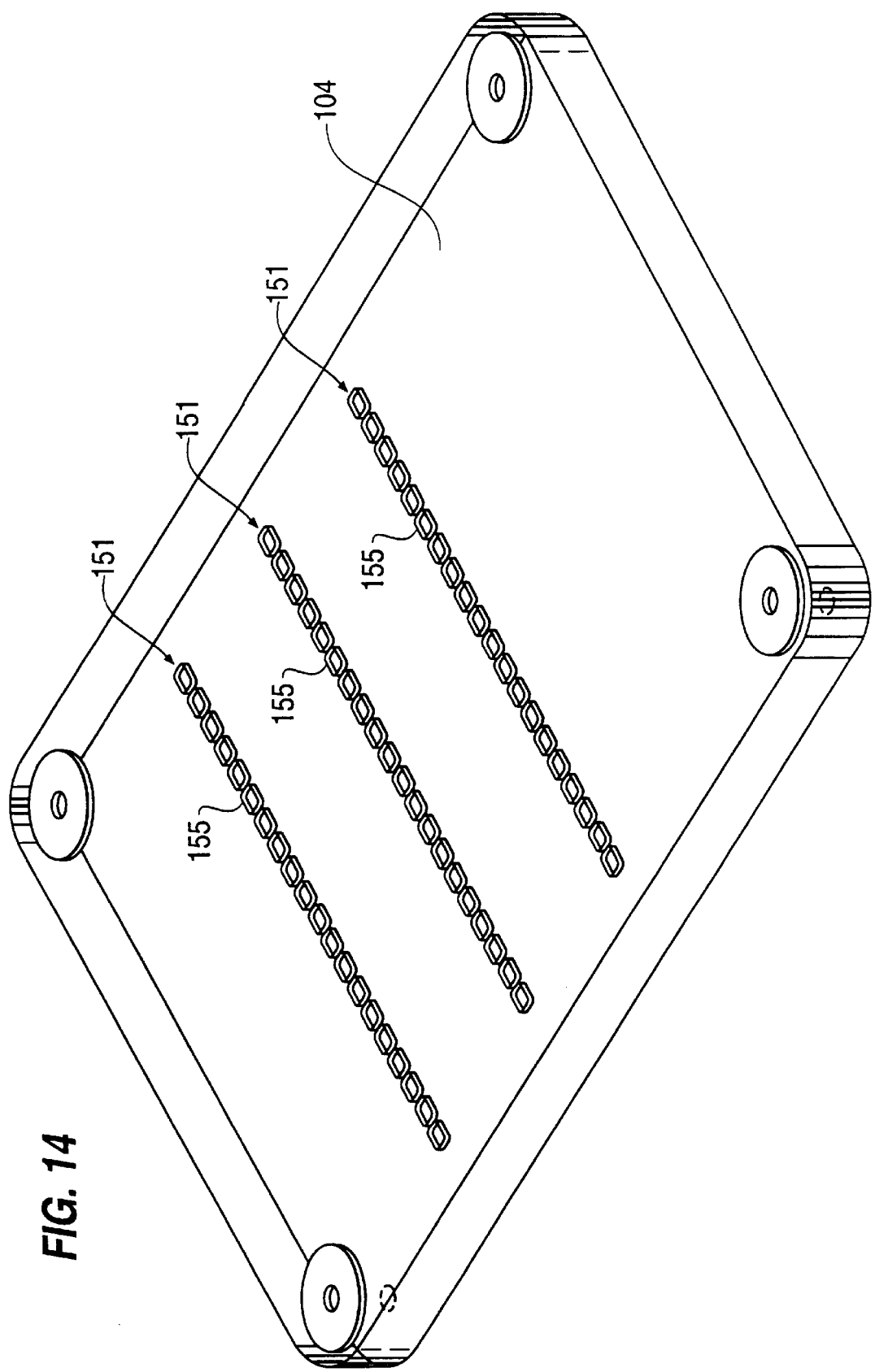
FIG. 14 is a perspective view of an alternative supply tray.

FIG. 14 shows a preferred supply tray 104. In this embodiment, the supply tray 104 has three rows 151 of evenly spaced receptacles 155. The size and spacing of the receptacles 155 depends on the size and spacing of the multiple applicator tip assembly 122. Preferably, the receptacles 155 are large enough to accommodate one or more applicator tips 130 and deep enough to insert the entire second portion 144 of the applicator tip 130. The supply tray 104 with rows 151 of individual receptacles 155 is preferred because each row and receptacle 155 may be filled with a different sample fluid. Thus, supply tray 104 is capable of testing more fluids simultaneously than supply tray 102. For example, the preferred supply tray 104 may contain three rows 151 and each row 151 may include eighteen receptacles 155. Eighteen receptacles 155 in each row 151 allows each row to contain fluid samples from three different patients. Each patient is allotted six receptacles 155 to allow each patient's blood to be tested with six different chemicals (for example serum and antisera).

Figure 15:
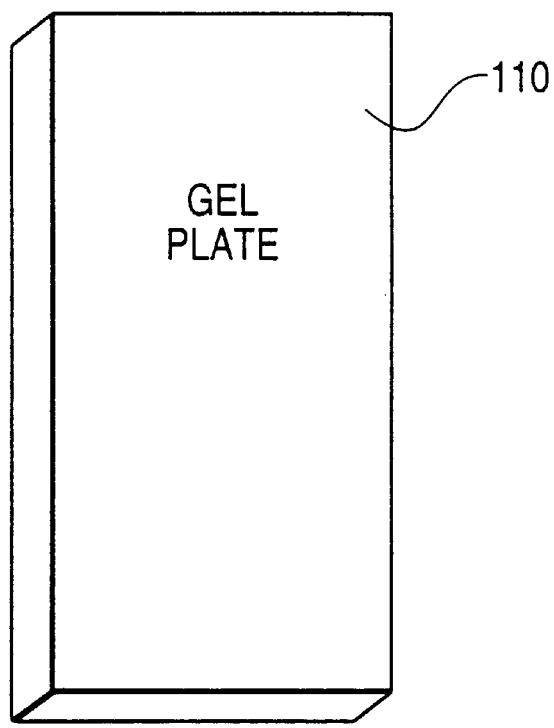
FIG. 15 is a perspective view of a substrate or gel plate.

FIG. 15 shows a substrate or gel plate 110. In the preferred embodiment, the gel plate 110 is made out of agarose gel. The substrate 110 should be large enough to receive the fluid samples and be subjected to electrophoresis. For examples of gel plates see U.S. Pat. No. 4,892,639, issued Jan. 9, 1990, entitled "ELECTROPHORESIS PLATE AND METHOD OF MAKING THE SAME"; U.S. Pat. No. 4,975,173, issued Dec. 4, 1990, entitled "ELECTROPHORESIS PLATE AND MAKING OF THE SAME"; and U.S. Pat. No. 5,045,164, issued Sep. 3, 1991; entitled "ELECTROPHORESIS PLATE FOR DIVERTING GENERATED FLUID", all of which are herein incorporated by reference.

In operation, the fluid applicator 106 is moved to a position above the supply tray 102, 104 with the application tips aligned above the channel 114. The applicator tips 130 are then inserted, dunked, or dipped into the receptacles by movement of the applicator holder 118. During the "dunking" process, the applicator tips 130 retain a quantity of the fluid sample from the channel 114 or receptacle 155. (The fluid sample is not shown in FIG. 12 or 13). Following the "dunking" procedure, the applicator 106 is removed from the channel 114 or receptacle 155 by the applicator holder 118, moved towards the substrate 110 and lowered in the vertical direction onto the substrate 110 to release the retained fluid.

B. Application Station

As stated above, an application station is a semiautomatic or automatic device for insuring precise deposit of the fluid sample on the substrate 110. The application station comprises three main components: a base, applicator guide, and applicator rack.

Figure 16:
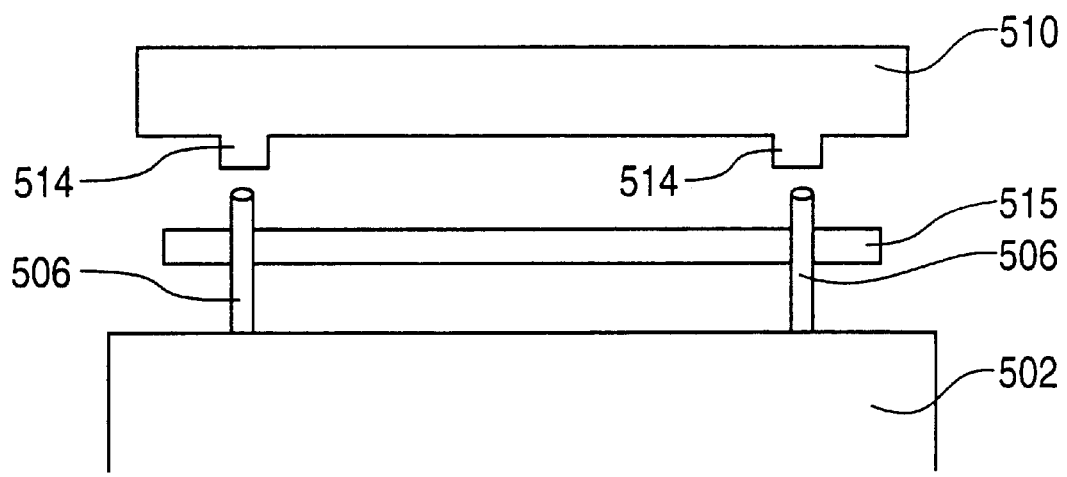
FIG. 16 is a side view of the base and the applicator guide within the application station.

FIG. 16 shows a side view of the base 502 and applicator guide 510 portions of the application station. The base 502 is flat solid structure which can be made of metal, hard plastic, wood, or any sturdy material. The base 502 is usually rectangular with four columns or pillars 506, but could take almost any shape or contain any number of pillars 506. In the preferred embodiment, the base is approximately five to seven inches wide, a half inch to two inches high, and five to seven inches long. The pillars 506 protruding from the base 502 connect the base 502 to the applicator guide 510 by fitting within the applicator guide's feet 514. The applicator guide's feet 514 are usually female ends designed to accept the pillars 506. The base 502 and applicator 510 are shown as two separable components, but these components could be constructed in a variety of different configurations. In other words, the base 502 and applicator guide 510 may be a single unit.

FIG. 16 also shows a substrate or gel plate 515 in between the base 502 and applicator guide 510. The substrate 515 is a flat plate approximately the same size as the base 502 with four holes corresponding to the four pillars 506 protruding from the base 502. The pillars 506 pass through the substrate 515 to hold the substrate 515 in place during application. In an alternative embodiment, the substrate 515 may be smaller than the base 502 and fit inside an indentation in the base 502.

Figure 17:
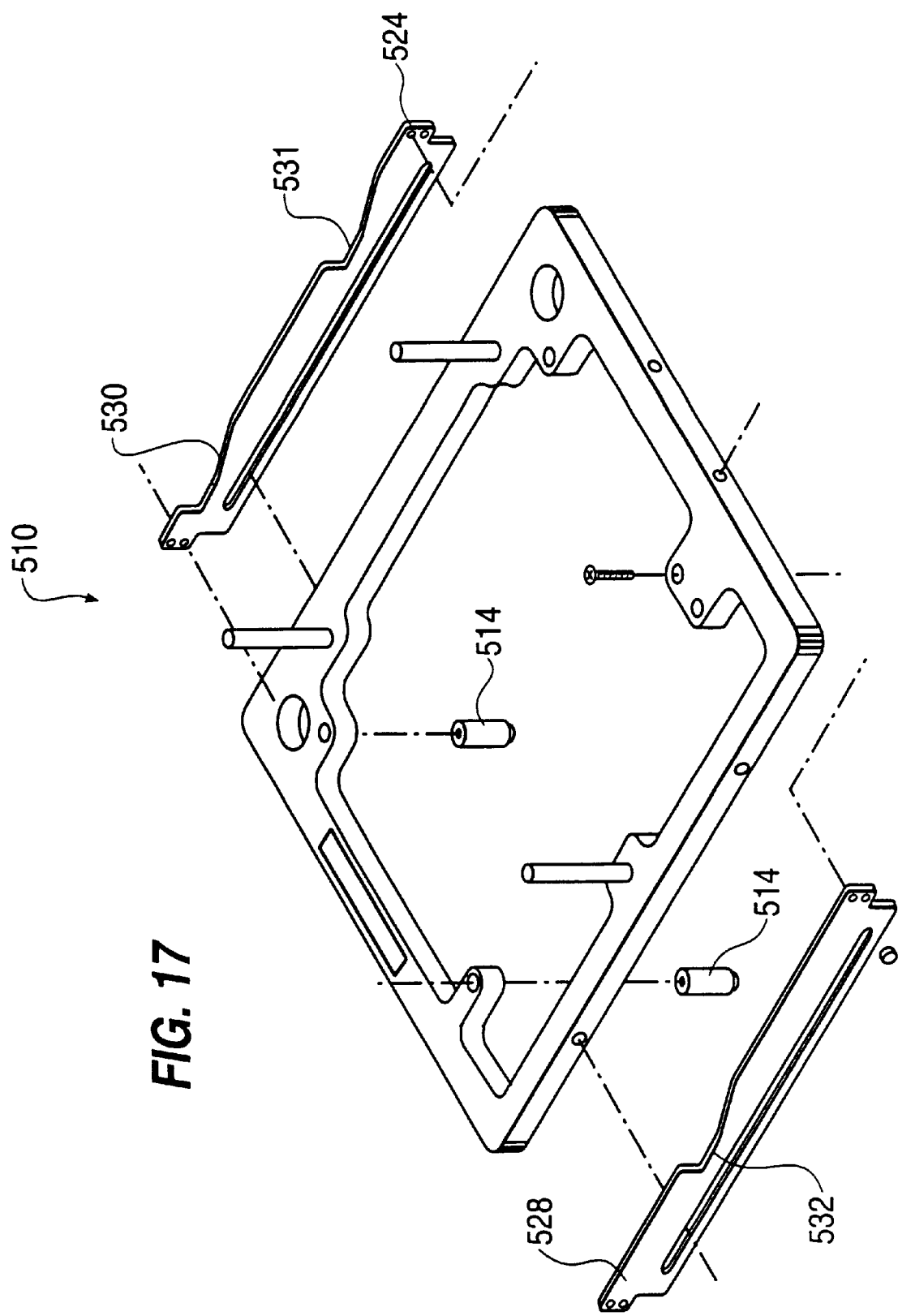
FIG. 17 is a perspective view of the applicator guide.

FIG. 17 shows a top view of the applicator guide 510. The applicator guide 510 is designed to control the application of biological fluids and other chemicals onto the substrate 515. The applicator guide 510 controls these applications with the two tracks 524, 528 positioned in parallel. The tracks 524, 528 are used to control the speed and location in which the fluids, chemicals or substances are deposited onto the substrate 515. The tracks 524, 528 control the location in which a fluid is deposited because they are designed to hold the applicator rack in a first position and a second position. In the first position, the tracks 524, 528 hold a fluid applicator 106, usually mounted in an applicator rack, above the substrate. In the second position, the tracks 524, 528 hold the fluid dispenser in a position closer to the substrate. The position closer to the substrate is designed to hold the fluid applicator 106 in a position which will cause the surface tension of the retained fluid to break. Thus, the fluid is released and deposited on the substrate.

In the preferred embodiment, the tracks 524, 528 control the movement of the fluid applicator 106 with three slides 530, 531, 532. The right track 524 has two slides 530, 531, one located near each end, and the left track 528 only has one slide 532 in the middle of the track 528. In alternative embodiments, the two tracks 524, 528 can have the same number of slides in the same location or a variety of other configuration. As stated above, the feet 514 are used to connect the applicator guide 510 to the base 502.

Figure 18:
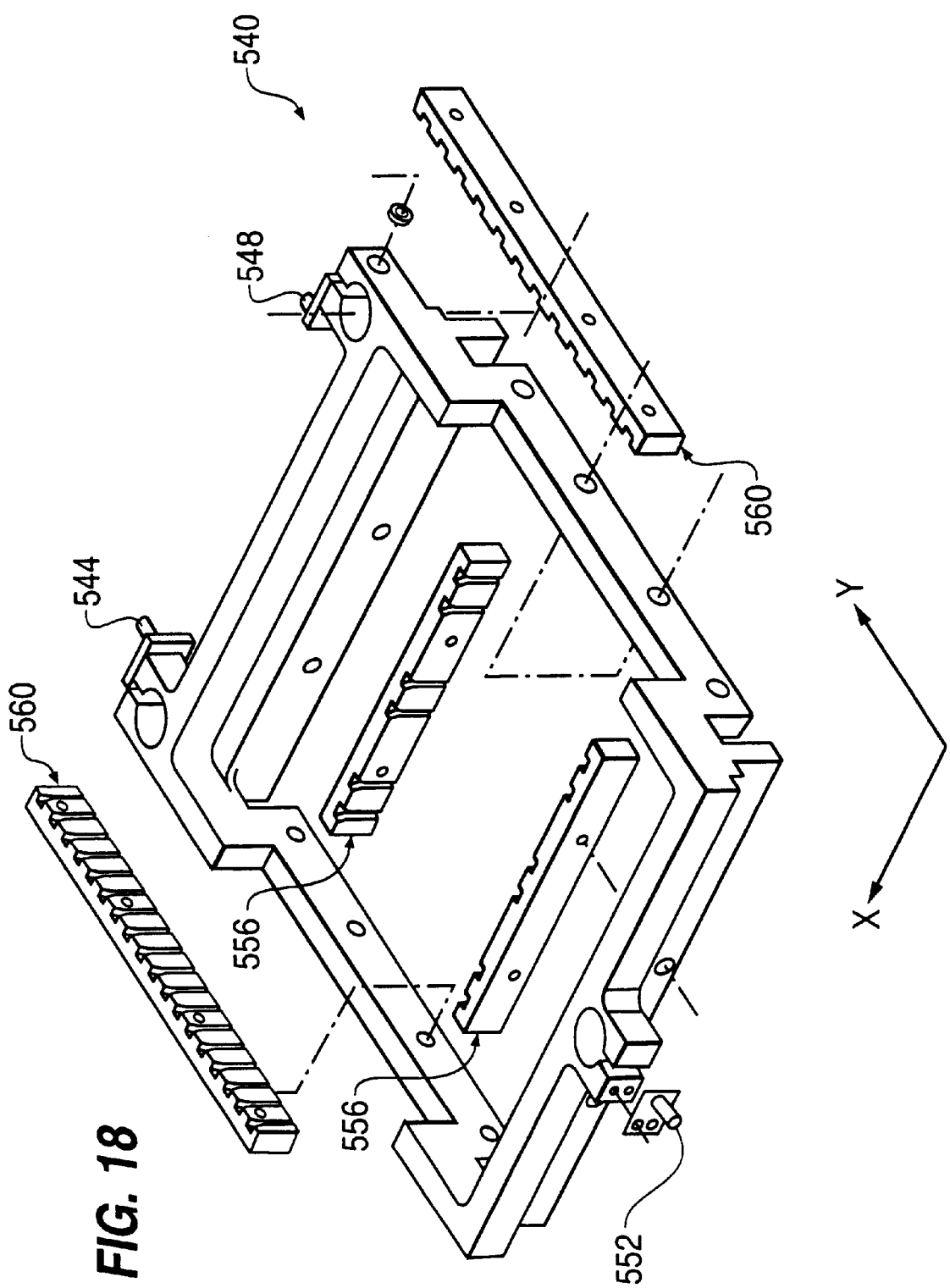
FIG. 18 is a perspective view of the applicator rack.

FIG. 18 shows an applicator rack 540 for use with the applicator guide 510. The rack applicator 540 has a right front post 544, a right rear post 548, and a left post 552. The applicator rack 540 may be attached to the applicator guide 510. The right front post 544 is designed to align with the applicator guide's right front slide 530. The right rear post 548 is designed to align with the applicator guide's right rear slide 531, and the left post 552 is designed to align with the applicator guide's left slide 532. In the preferred embodiment, each post is aligned with its corresponding slide, and slowly lowered in the vertical direction. The sliding or lowering of the applicator rack 540 from top of the slide to the bottom causes the applicator 106 and applicator tip 130 to move from a position above the substrate 515 to a position in contact with the substrate 515. When the applicator tip 130 contacts the substrate 515, it breaks the surface tension between the fluid and the applicator tip 130. When the surface tension is broken, the fluid carried on the applicator tip 130 is deposited on the substrate 515. The applicator tip 130 does not necessarily have to contact the substrate 515 to break the surface tension. The applicator guide 510 and applicator rack 540 are designed to minimize the contact and prevent any damage to the substrate 515.

The slides 530, 531, 532 are also used to improve the control over the speed in which the applicator rack 540 is lowered onto the substrate 515. The slides 530, 531, 532 improve the control because they create friction. The friction slows the dissent of the applicator rack 540. In an alternative embodiment, slides 530, 531, 532 are not required. The applicator rack 540 may simply be lowered in the vertical direction. In another alternative embodiment, the applicator rack 540 may contact the substrate by moving in a circular path.

The applicator rack 540 also has a first set of slots 556 and a second set of slots 560 for holding applicators. Each set of slots contacts a plurality of individual pairs of slots. The slots 556, 560 are designed to hold guides 170, 174, like the ones shown in FIG. 1. These slots 556, 560 may differ in size or shape to insure the applicator 106 is properly inserted. In the embodiment shown, the first set of slots 556 is able to hold six applicators 106 simultaneously because it has six individual slots. However, the preferred operation of the system is to leave an empty slot between each applicator 106, limiting the number of applicators 106 inserted simultaneously to three.

The second set of slots 560 includes twelve individual slots. These slots are used to hold chemical dispensers, sera dispensers or other applicators containing chemicals (some of which may improve the visibility of the results achieved from immuno-fixation electrophoresis).

In the embodiment shown in FIG. 18, the first set of slots 556 is positioned perpendicular to the second set of slots 560. This configuration is designed to facilitate use of the application station for different types of electrophoresis, including immuno-fixation electrophoresis. Specifically, the first set of slots 556 are designed to deposit the biological fluid in a "two dimension" line in the X direction. The two dimensional line is achieved by inserting an applicator 106 into the first set of slots 556, aligning the applicator rack 540 with the slides 530, 531, 532 in the applicator guide 510; lowering the applicator rack 540 along these slides; and depositing the fluid retained on the applicator tip 130 onto the substrate 515. The deposit is approximately a two dimensional line because of the shape of the tip.

Once the fluid is deposited on the substrate 515, electrophoresis is performed. Electrophoresis causes the molecules deposited in the two dimensional line to migrate in a direction perpendicular (i.e., Y direction) to the two dimensional line created by the deposited fluid.

After the electrophoresis is completed, a second applicator 106 is loaded in the second set of slots 560. Then the second applicator 106 is lowered to dispense chemicals in the Y direction, perpendicular to the originally deposited fluid. Since as a result of the electrophoresis, the molecules migrated in the Y direction, the chemicals are dispensed perpendicularly to the original deposit in the X direction.

Also, in the embodiment shown in FIG. 18, the first set of slots 556 and the second set of slots 560 are both aligned in the XY plane. Thus, the applicator rack 540 should not be loaded with applicators 106 in the first set of slots 556 and applicators 106 in the second set of slots 560 at the same time. One of the advantages of this configuration is that it decreases the size of the application station. However, in alternative embodiments, applicators and dispensers can be loaded in the first set of slots and the second set of slots simultaneously.

In an alternative embodiment, two sets of slots can be used simultaneously. The first set of slots 556 and a second set of slots 560 are positioned far enough apart along the line of movement of the rack (along the tracks), that the two sets of slots 556, 560 do not interfere with each other during use. In this manner, two sets of applicators can be loaded, one in each set of slots, and remain loaded during an entire procedure. The slides are configured in such a manner that the rack would travel along the slides, deposit fluids from the first set of applicators and then be moved so that the fluids on the second set of applicators could be lowered vertically and placed on the substrate (without interference from the first set of applicators). Preferably, the rack for this embodiment is larger in the direction of movement and the slides to support such a larger rack are longer than the rack 540 used in the preferred embodiment.

Some of the steps for using the application station or fluid applicator 106 may include: placing the substrate or gel plate 515 into the application station; connecting the application guide 510 to the base 502; inserting a first applicator 106 into the applicator rack 540, usually in the first set of slots 556; aligning the pillars 506 of the applicator rack 540 including the first applicator with the applicator guide 510; lowering the applicator rack 540, including the first applicator 106, onto the substrate 515; raising the applicator rack 540, including the first applicator 106 away from the substrate 515; removing the first applicator 106 from the applicator rack 540; removing the substrate 515; performing electrophoresis on the fluid deposited on the substrate 515; reinserting the substrate 515 into the application station; installing a second applicator or dispenser 106 into the applicator rack 540, usually in the second set of slots 560; realigning the applicator rack 540 with the applicator guide 510; applying the second applicator 106 using the applicator rack 540 onto the results of the electrophoresis; raising the second applicator 106 using the applicator rack 540; removing the substrate 515 treated with the chemical or substance from the second applicator 106; and viewing the results. Electrophoresis may also be performed on the substrate while the substrate is on the base beneath the racks.

C. Chemical Delivery System

In many chemical delivery systems for delivering chemicals or substances to test samples, there are problems associated with the volume of chemicals delivered and the control of the delivery. Specifically, there are problems delivering a known quantity of the chemicals to a precise location on a substrate or sample located on a substrate. Many times, the test sample lanes on the substrate are small, in the range of 1 mm to 5 mm wide. Also, because of factors such as fluid viscosity and adhesion coefficients, the volume of the chemical being delivered may prematurely or spontaneously unload and drip prior to delivery. Delivery applicators in the prior art have these and related problems.

Figure 19:
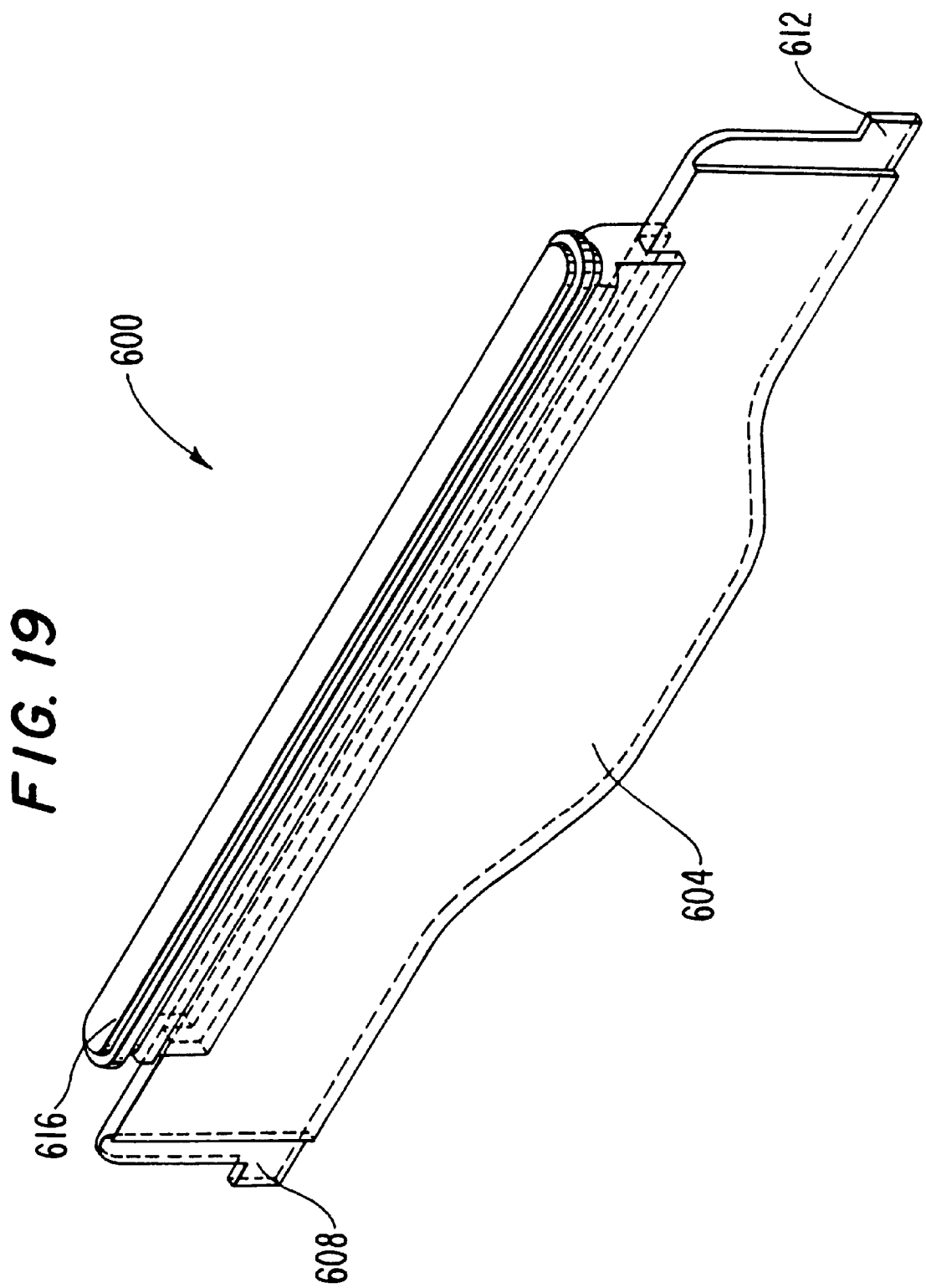
FIG. 19 is a perspective view of a chemical delivery system applicator.

FIG. 19 shows a delivery system applicator 600. The delivery system applicator 600 includes a delivery system applicator holder 604 with a left guide 608, a right guide 612, and a reservoir 616.

The delivery system holder 604 may be constructed similar to the sample fluid applicator holder 118. The delivery system applicator holder 604 can be constructed of a plastic, such as styrene, or other materials known in the art. The right and left guides 608, 612 may be made identical and symmetrical or, may be shaped differently so that the holder 604 can only be aligned or placed in the applicator rack 540 in one direction or position. The left and right guides 608, 6122 may be constructed similar to the guides in the sample fluid applicator 106 described above.

The reservoir 616 is preferably an elongated well or tunnel-shaped reservoir. The reservoir 616 has an opening preferably located at the bottom and away from the delivery applicator holder 604. The reservoir 616 may be made from a variety of materials including those from which the applicator holders 604, 118, are constructed. The reservoir 616 is connected to the holder 604. A variety of methods may be used for connecting the reservoir to the holder, including a snap fit plastic connection, adhesives (such as glue or tape), screws or fasteners, heat weld, ultrasonic sealing, etc. Many of the methods described above for connecting the multiple applicator tip assembly 122 to the applicator holder 118 can also be used to connect the reservoir 616 to the delivery system holder 604.

Preferably, the reservoir 616 is shaped or formed to hold a gel or "gel-like" substance. Various configurations are possible for the reservoir, including with lips or ledges around the edge of the reservoir and other structures within the reservoir 616 to assist in keeping the gel held within the reservoir 616.

A variety of fluid retaining substances (such as gel forming substances) may be used in the reservoir 616 of the delivery system 600. Some examples are polymers, gels, agarose, polysaccharide, carrageenan, and other fluid retaining substances that have the consistency necessary to be effectively used in the reservoir 616.

A variety of chemicals or fluids may be delivered using the disclosed delivery system 600. For example, serum protein and antiserums may be delivered using the delivery system 600. The serum proteins and antiserums are held by the fluid retaining substances in the reservoir 616.

In operation, it is preferred that a mixture of the chemical or fluid to be delivered and the fluid retaining substance is made and poured, cast or placed in the reservoir 616 where it congeals and is held or adhered to the reservoir 616. Although various methods for the reservoir 616 to hold the fluid retaining substance and chemical or fluid are possible, it is preferred that the chemical and fluid retaining substance are cast (together) into the reservoir 616 where the cast itself holds the fluid retaining substance and chemical in place. Other methods may be used for holding the fluid retaining substance and chemical in the reservoir 616: including shaping the reservoir 616 so as to hold the fluid retaining substance (and chemical) such as with lips or ledges running along the perimeter of the reservoir 616, adhesives, or other methods. Generally, the delivery system 600 is loaded with fluid retaining substance and fluid or chemical when it is in an inverted or upside down position. Loading the fluid retaining substance and fluid in this manner allows it to gel in place within the reservoir before the forces of gravity begin to pull on it and pull it away from the reservoir 616. This pre-loading of the chemical or fluid eliminates the need for a dunking step.

In use, the applicator 600 is preferably held in an upright position by semiautomatic or automatic chemical delivering device. Such a device, several of which are herein disclosed, would use the guides 608, 612 to hold the delivery system applicator 600 in place during the delivery process. The device brings the delivery system applicator 600 towards the substrate 110, 515 and creates a contact between the substrate and the delivered chemical and/or fluid retaining substance in the reservoir 616. When the "gel-like" substance in the reservoir makes contact with the substrate, a controlled volume of chemical or fluid is delivered to the substrate. Using this delivery method the delivered chemical or fluid can also be placed in a precise location on the substrate.

With regard to using the following apparatuses and methods in an automated immuno-fixation electrophoresis process using six chemical sample treatments, the following information applies. For general information on the automated immuno-fixation electrophoresis process, see U.S. Pat. No. 5,137,614 entitled "IMMUNOFIXATION ELECTROPHORESIS CONTROL SYSTEM", issued on Aug. 11, 1992, hereby incorporated by reference.

In the preferred embodiment, the six chemical treatment tests are performed as follows.

The first test is an analysis of total serum protein (SP) and the remaining five tests are each used in the detection of a different protein. This is conventional in an IFE process.

The six tests are usually a total serum protein test [designated SP] followed by tests for the presence or absence of the monoclonal immunoglobulins IgG, IgA, IgM, Kappa and Lambda [designated G, A, M, K and L, respectively].

For the serum protein test, it is preferred that the fluid retaining substance be carrageenan. More specifically, the preferred serum protein fixative is 10% acetic acid, 5% sulfosalicylic acid and 1% tannic acid. In the preferred method, this serum protein fixative (10% acetic acid, 5% sulfosalicylic acid, 1% tannic acid) is mixed with 2% carrageenan and then, the entire solution is diluted by one half. Therefore, in the final solution for the reservoir 616, approximately 1% carrageenan is preferred.

The remaining five tests (tests number 2–6), use antisera. Each antisera [tests 2–6, G, A, M, K, and L] is mixed with a 2% low melting point agarose so that the final concentration of the solution is 7.5 milligrams per milliliter [mg/ml].

While carrageenan, a polysaccharide is preferred for the serum protein test (as the fluid retaining substance or polymer), it is preferred that the antisera tests use agarose as the fluid retaining substance or polymer with each respective antisera.

III. An Automatic System

The methods and techniques of the present invention can also be performed automatically. FIG. 20 shows an example of an automatic immuno-fixation electrophoresis system 200 which automates the methods and techniques. The system has seven stations. The seven stations are: sample applicator station 301; electrophoresis station 302; antisera or chemical delivery station 303; first drying fan station 305; wash station 304; second drying fan station 306; and stain/destain station 307.

The system is initiated when a carrier is inserted in the entrance 300. The carrier is a metal or plastic sheet or tray which is designed to move between the stations. The mechanics which move the carrier can be configured a variety of ways, including a conveyor or other motorized delivery system 309. The timing of the movements is controlled with a preprogrammed microprocessor. For example, when a carrier is inserted in the entrance and the system is initiated, the preprogrammed microprocessor instructs the motorized delivery system 309 to move the carrier into the applicator station 301.

The applicator station 301 receives the carrier, selects a fluid sample with a fluid applicator from a sample tray; deposits the sample on the substrate; and forwards the carrier to the electrophoresis station 302. Specifically, at the instruction of a preprogrammed microprocessor, a motorized device lowers the fluid applicator to retain the sample, moves the fluid applicator to a position above the substrate, lowers the fluid applicator to deposit the retained fluid on the substrate, and returns the fluid applicator to its home position.

Then the carrier is moved to the electrophoresis station 302. At the electrophoresis station 302, the fluid sample is separated into its component molecules with electrophoretic techniques.

Next, the carrier is moved to the antisera station 303. At the antisera station 303, a substance or chemical delivery applicator is used to automatically apply a substance or chemical to the separated molecules. Generally, these substances are designed to enhance the visibility of certain molecular structures. Similar to the sample applicator station 301, the chemical delivery applicator is connected to a motorized apparatus which automatically moves the applicator through the necessary steps to apply the substance. Preferably, the chemicals are "pre-loaded" onto the chemical delivery applicator and therefore, no dunking step is necessary.

After the substance or chemicals are applied, the carrier may be moved to the first wash station 304 and the first drying fan station 305. After the first drying station 305, the carrier may be moved to the stain/destain station 307, followed by the second drying station 306, and exit 308.

The foregoing description of the present invention has been presented for purposes of illustration and description. The description is not intended to limit the invention to the forms described. Variations and modifications commensurate with the above teachings, and within the skill and knowledge of the relevant art, are part of the scope of the present invention.

What is claimed is:

1. An apparatus for transferring a fluid from a supply to a substrate comprising:
    an applicator holder, and
    at least one applicator tip, connected to the holder, comprising a barrier, wherein the applicator tip retains fluid below the barrier and the barrier controls the amount of fluid deposited on the substrate, and further characterized by at least one of the following (a) through (e);
        (a) the barrier is selected from the group consisting of a physical barrier, at least one aperture, and a rough surface;
        (b) the applicator tip has a first portion and a second portion, the first and second portions are made of a material selected from the group consisting of nylon and polyester, and the second portion has a surface which is metalized to retain fluid;
        (c) the applicator tip has a first portion and a second portion, the first portion is generally lyophobic;
        (d) the applicator tip has a first portion and a second portion, the second portion is generally lyophilic;
        (e) the applicator tip has a first portion and a second portion, the second portion has a higher affinity to retain fluid by surface tension than the first portion.

2. The apparatus of claim 1, wherein the barrier limits the amount of fluid retained.

3. The apparatus of claim 1, wherein the apparatus includes a plurality of applicator tips.

4. An apparatus according to claim 1, and further comprising a base;
    an applicator guide, connected to the base, wherein the applicator guide has at least one track; and
    an applicator rack alignable with the applicator guide comprising a pair of slots whereby the pair of slots holds said applicator, the at least one track holds the pair of slots in a first position and a second position, and the second position is closer to the substrate than the first position.

5. The apparatus of claim 4, wherein the applicator guide has a first track and a second track and wherein the first and second tracks are parallel to each other.

6. The apparatus of claim 4, wherein the first track and the second track each include at least one slide and wherein the pair of slots moves from the first position to the second position by sliding down the slides.

7. The apparatus of claim 6, wherein the applicator rack has at least two posts and the posts align with the slides.

8. The apparatus of claim 7, wherein the base and applicator guide are one piece.

9. The apparatus of claim 8, where in the base, applicator guide, and applicator rack are all one piece.

10. The apparatus of claim 4, wherein the pair of slots is one of a first set of slots and whereby the first set of slots can hold several applicators simultaneously.

11. The apparatus of claim 10, wherein the applicator rack further comprises a second set of slots aligned perpendicular to the first set of slots, whereby the first pair of slots can also hold several applicators simultaneously, and wherein the second set of slots are also held in a first and second position.

12. The apparatus of claim 11, wherein the second set of slots are held above the substrate in the first position and closer to the substrate in the second position.

13. The apparatus of claim 10, wherein the first set of slots holds a cartridge which holds a plurality of applicators.

14. The apparatus of claim 10, wherein the base, applicator guide, and applicator rack are components of an application station and wherein the application station is used in immuno-fixation electrophoresis.

15. The apparatus of claim 4, wherein the pair of slots includes a first slot and a second slot and wherein the first slot is larger than the second slot.

16. The apparatus of claim 4, wherein the pair of slots holds a fluid applicator.

17. The apparatus of claim 4, wherein the pair of slots are moved from the first position to the second position electrically.

18. The apparatus of claim 4, wherein the pair of slots moves from the first position to the second position by moving in a vertical direction.

19. The apparatus of claim 4, wherein the substrate is held between the base and the applicator guide.

20. The apparatus of claim 4, wherein the pair of slots moves in a circular path from the first position to the second position.

21. The apparatus of claim 1, and further comprising:
a reservoir, connected to the applicator holder, comprising a fluid retaining substance; and
fluid dispersed in the fluid retaining substance, wherein the fluid retaining substance delivers the dispersed fluid onto the substrate after contact is made between with the fluid retaining substance and the substrate.

22. The apparatus of claim 21, wherein the reservoir is an elongated well.

23. The apparatus of claim 21, wherein the reservoir is tunnel-shaped and a portion of the fluid retaining substance is held in the tunnel-shaped reservoir.

24. The apparatus of claim 21, wherein the reservoir comprises an opening from which a portion of the fluid retaining substance protrudes and the protruding fluid retaining substance is brought into contact with the substrate.

25. The apparatus of claim 24, wherein the opening opens away from the direction the holder is connected to the reservoir.

26. The apparatus of claim 21, wherein the fluid retaining substance is poured into the reservoir.

27. The apparatus of claim 21, wherein the fluid retaining substance is cast into the reservoir.

28. The apparatus of claim 21, wherein the fluid retaining substance adheres to the reservoir.

29. The apparatus of claim 21, wherein the fluid retaining substance traps the fluid.

30. The apparatus of claim 21, wherein the fluid retaining substance delivers the fluid to the substrate by releasing the fluid upon contact with the substrate.

31. The apparatus of claim 21, wherein the fluid retaining substance is a polymer.

32. The apparatus of claim 31, wherein the polymer is a gel.

33. The apparatus of claim 32, wherein the gel is agarose.

34. The apparatus of claim 31, wherein the polymer is polysaccharide.

35. The apparatus of claim 31, wherein the polymer is carrageenan.

36. The apparatus of claim 21, wherein the fluid is serum protein.

37. The apparatus of claim 21, wherein the fluid is antiserum.

38. The apparatus of claim 21, wherein the holder comprises first and second guides.

39. The apparatus of claim 38, wherein the first guide and second guide are of different thickness.

40. The method of claim 39, further comprising the step of disposing the polymer after the polymer has been contacted with the substrate.

41. The apparatus of claim 21, further comprising a cartridge which connects the holder to a second holder.

42. The apparatus of claim 1, wherein the applicator holder further comprises a first guide and a second guide, wherein the first guide is larger than the second guide.

43. A method for transferring a fluid from a supply to a substrate comprising:
inserting an applicator with an applicator tip into a supply to retain fluid, wherein the applicator tip has a barrier and a distal end;
removing the applicator from the supply, wherein the applicator tip retains fluid only between the barrier and the distal end;
moving the applicator tip with the retained fluid toward the substrate; and
depositing the retained fluid on the substrate, and the applicator further characterized by at least one of the following (a) through (e);
(a) the barrier is selected from the group consisting of a physical barrier, at least one aperture, and a rough surface;
(b) the applicator tip has a first portion and a second portion, the first and second portions are made of a material selected from the group consisting of nylon and polyester, and the second portion has a surface which is metalized to retain fluid;
(c) the applicator tip has a first portion and a second portion, the first portion is generally lyophobic;
(d) the applicator tip has a first portion and a second portion, the second portion is generally lyophilic;
(e) the applicator tip has a first portion and a second portion, the second portion has a higher affinity to retain fluid by surface tension than the first portion.

44. The method of claim 43, wherein the substrate includes a gel onto which the retained fluid is transferred, the method further comprising:
electrophoresing the deposited fluid to separate molecules within, the deposited fluid.

45. The method of claim 44, further comprising applying chemicals to the separated molecules to enhance visibility of the separated molecules.

46. The method of claim 44, wherein the fluid is a biological fluid.

47. The method of claim 46, wherein the biological fluid is blood.

48. The method of claim 44, wherein the gel is an agarose gel.

49. The method of claim 44, wherein the electrophoresis is an immuno-fixation electrophoresis.

50. The method according to claim 43, and further comprising the steps of:
placing a substrate between a base and an applicator guide;
aligning an applicator rack, including at least one applicator retaining fluid, with the applicator guide;
inserting at least one applicator retaining fluid into the applicator rack;
and wherein said step of depositing the retained fluid comprises lowering the applicator rack within the applicator guide until the fluid retained on the at least one applicator is deposited on the substrate; and
raising the applicator rack away from the substrate.

51. The method of claim 50, further comprising the steps of:
removing the applicator from the applicator rack;
installing a dispenser retaining a chemical in the applicator rack; and lowering the applicator rack within the applicator guide until the chemical in the dispenser is deposited on the substrate.

52. The method of claim 50, further comprising the step of:

performing electrophoresis on the deposited fluid.

53. The method of claim 52, wherein the electrophoresis performed is immuno-fixation electrophoresis.

54. The method of claim 43, further comprising:

loading a polymer with the fluid;

said applicator holder having a reservoir and the polymer; and contacting the substrate with the polymer whereby the loaded fluid is deposited on the substrate.

55. The method of claim 54, wherein the step of loading comprises entrapping the fluid in the polymer.

56. The method of claim 54, wherein the step of loading comprises:

mixing the polymer and the fluid; and pouring the polymer and the fluid into the reservoir.

57. The method of claim 54, wherein at least a portion of the polymer is located inside the reservoir, the polymer and the fluid form a gel, and further comprising casting the gel in the reservoir.

58. The method of claim 54, further comprising the step of removing the polymer from contact with the substrate after sufficient fluid has been delivered to the substrate.

* * * * *